(12) United States Patent
Cho et al.

(10) Patent No.: US 7,130,687 B2
(45) Date of Patent: Oct. 31, 2006

(54) IMPLANTABLE MEDICAL DEVICE AND METHOD FOR DELIVERING THERAPY FOR SLEEP-DISORDERED BREATHING

(75) Inventors: Yong K. Cho, Maple Grove, MN (US); H. Toby Markowitz, Roseville, MN (US)

(73) Assignee: Medtronic, Inc, Minneapolis, MN (US)

( * ) Notice: Subject to any disclaimer, the term of this patent is extended or adjusted under 35 U.S.C. 154(b) by 453 days.

(21) Appl. No.: 10/693,375

(22) Filed: Oct. 24, 2003

(65) Prior Publication Data

US 2005/0090871 A1 Apr. 28, 2005

(51) Int. Cl.
*A61N 1/362* (2006.01)

(52) U.S. Cl. .................. 607/17; 607/2; 607/9; 607/19; 607/20; 607/24; 607/25; 607/42; 600/29; 600/483; 600/484; 600/523

(58) Field of Classification Search .......... 607/17, 607/42, 19–20, 24–25, 2, 9, 1; 600/529, 600/484, 483, 509, 519, 515, 513, 523, 29
See application file for complete search history.

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,384,585 A | 5/1983 | Zipes | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,380 A | 2/1988 | Vollmann et al. | |
| 4,727,877 A | 3/1988 | Kallok | |
| 4,800,883 A | 1/1989 | Winstrom | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |
| 5,117,824 A | 6/1992 | Keimel et al. | |
| 5,163,427 A | 11/1992 | Keimel | |
| 5,188,105 A | 2/1993 | Keimel | |
| 5,213,098 A | 5/1993 | Bennett et al. | |
| 5,345,362 A | 9/1994 | Winkler | |
| 6,126,611 A | 10/2000 | Bourgeois et al. | |
| 6,223,072 B1 | 4/2001 | Mika et al. | |
| 6,233,484 B1 | 5/2001 | Ben-Haim et al. | |
| 6,233,487 B1 | 5/2001 | Mika et al. | |
| 6,263,242 B1 | 7/2001 | Mika et al. | |
| 6,292,693 B1 | 9/2001 | Darvish et al. | |
| 6,298,268 B1 | 10/2001 | Ben-Haim et al. | |
| 6,317,631 B1 | 11/2001 | Ben-Haim et al. | |
| 6,424,866 B1 | 7/2002 | Mika et al. | |
| 6,459,928 B1 | 10/2002 | Mika et al. | |

(Continued)

FOREIGN PATENT DOCUMENTS

EP 0 940 155 B1 4/2004

(Continued)

*Primary Examiner*—Robert E. Pezzuto
*Assistant Examiner*—Deborah Malamud
(74) *Attorney, Agent, or Firm*—Girma Wolde-Michael; Daniel G. Chapik

(57) ABSTRACT

An implantable medical device delivers augmentation therapy to intervene in a pattern of sleep-disordered breathing. Augmentation therapy includes the delivery of electrical stimulation to cardiac tissue above and/or below a capture threshold. PESP and NES/CCM are possible augmentation therapies that are used alone or in combination. In addition, augmentation therapies can be used with other pacing therapies such as atrial overdrive pacing and atrial coordinated pacing as a therapy for sleep-disordered breathing.

73 Claims, 10 Drawing Sheets

U.S. PATENT DOCUMENTS

| | | |
|---|---|---|
| 6,463,324 B1 | 10/2002 | Ben-Haim et al. |
| 6,574,507 B1 * | 6/2003 | Bonnet .................. 607/20 |
| 2002/0193697 A1 | 12/2002 | Cho et al. ............... 600/529 |
| 2003/0023279 A1 | 1/2003 | Spinelli et al. |
| 2003/0153954 A1 | 8/2003 | Park et al. ............... 607/17 |

FOREIGN PATENT DOCUMENTS

| | | |
|---|---|---|
| WO | WO9218198 | 10/1992 |
| WO | WO0001438 | 1/2000 |

* cited by examiner

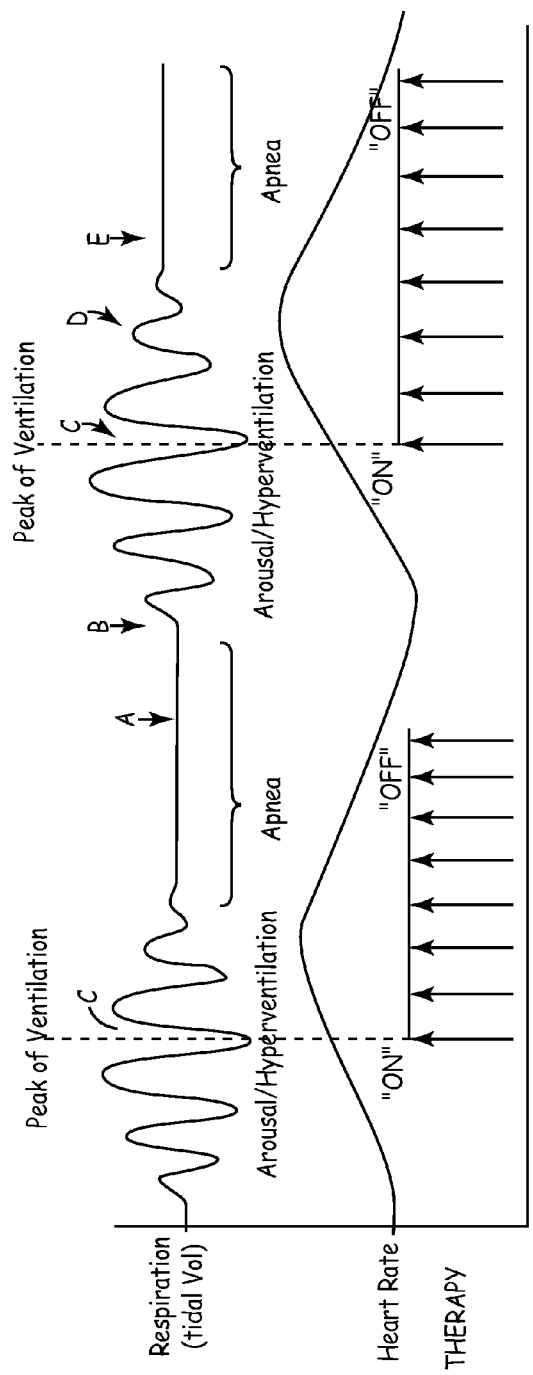
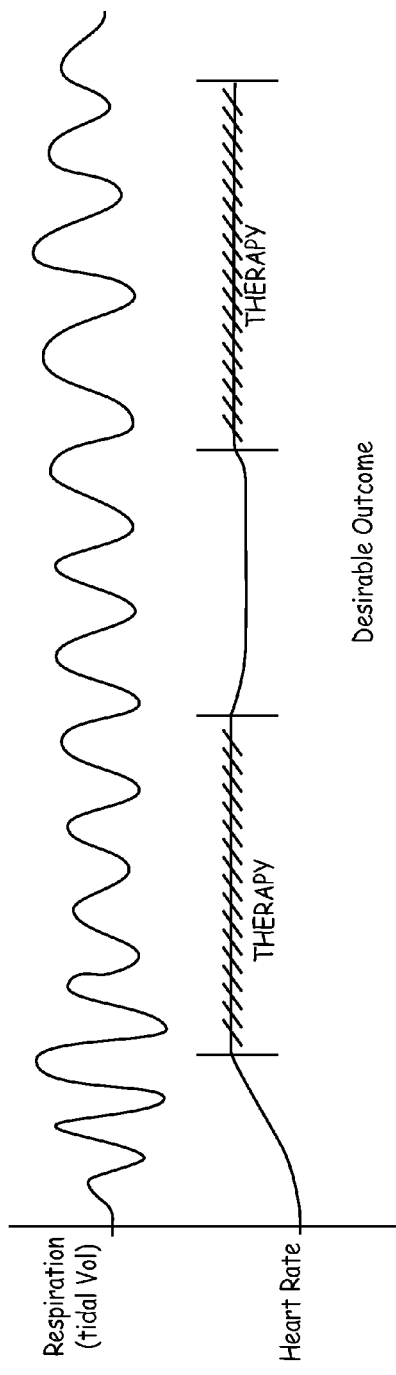
FIG. 4A
FIG. 4B

IMPLANTABLE MEDICAL DEVICE AND METHOD FOR DELIVERING THERAPY FOR SLEEP-DISORDERED BREATHING

BACKGROUND OF THE INVENTION

1. Field of the Invention

The present invention relates to implantable medical devices. More specifically, the present invention relates to implantable medical devices that deliver therapy to intervene in sleep-disordered breathing cycles.

2. Description of the Related Art

Sleep-disordered breathing encompasses a variety of conditions including, for example, central sleep apnea and obstructive sleep apnea. In both instances, a cessation of breathing (apnea) and/or shallow or slow breathing (hypopnea), occurs on an intermittent or periodic basis. The apnea is generally terminated by an arousal from sleep leading to a disturbance of the sleep pattern. Such interrupted sleep often causes excessive daytime sleepiness, depression, irritability, memory impairment, and headaches. In addition, sleep-disordered breathing can be life threatening and an increasing correlation between sleep-disordered breathing and hypertension, diabetes, stroke, arrhythmia, heart failure and heart attacks is being established.

Obstructive sleep apnea is the result of a blockage of a portion of the upper airway, usually associated with a relaxation in muscle tone and/or a reduction in the size of the airway due to, for example, excessive fatty tissue. This mechanical blockage creates a pressure differential that further facilitates the apnea.

Central sleep apnea is a neurological disorder, wherein normal breathing patterns are interrupted due to a failure of the brain to generate the proper muscle stimulation pulses. Once initiated, the resultant apnea is terminated with a resumption of respiration. Central sleep apnea can precede obstructive sleep apnea and this combination is referred to as mixed sleep apnea.

One particular variant of central sleep apnea that is often associated with patients suffering from chronic heart failure is Cheyne-Stokes respiration. Cheyne-Stokes respiration is a pattern of breathing characterized by a waxing and waning of tidal volume with complete cessation of breathing. Typically, a cycle of Cheyne-Stokes respiration lasts about 30–90 seconds. The cycle then repeats itself.

There are a variety of treatment options available for addressing sleep-disordered breathing. The most common treatment is the use of CPAP (Continuous Positive Airway Pressure). The patient generally wears an appliance such as a full facemask or more typically a nose covering mask or nasal inserts that deliver pressurized air into the airway to maintain the airway in an open state. The therapy is effectively a pneumatic stent. CPAP is generally effective at treating both central and obstructive apnea; however, many patients do not tolerate the therapy and discontinue its use.

Another method used to address sleep-disordered breathing involves atrial overdrive pacing (AOP). That is, an implantable medical device (IMD) is implanted to pace the heart. The pacing rate is elevated from a normal resting or sleeping rate (e.g., normal nocturnal intrinsic rate or a normal paced sleeping rate). For example, such techniques are described in U.S. Pat. No. 6,126,611, assigned to Medtronic, Inc., which is herein incorporated by reference in its entirety.

There are several timing scenarios for initiating AOP. For example, AOP can be delivered anytime a sleep state is detected or at predetermined intervals during sleep. Alternatively, AOP can be delivered when apnea is detected.

Similarly, there are various mechanisms for delivering specific AOP therapies. For example, once initiated the overdrive pacing can be set to a given higher rate, such as for example 3–5 beats/minute above normal, 10–12 beats/minute above normal, or even higher rates such as 30 beats/minute above normal. Alternatively, AOP can be initiated at a lower level above normal and gradually increased.

The use of AOP to address sleep-disordered breathing and its exact mechanisms are currently being investigated. The elevated pacing rate may lead to arousal such that apnea is terminated; however, it is believed more likely that the maintenance of heart rate and the increase in cardiac output achieved via AOP may positively affect autonomic tone sufficiently to reduce the overall number of apneas. While promising, the use of AOP does not always provide a successful therapy for sleep-disordered breathing.

SUMMARY OF THE INVENTION

The present invention, in one embodiment, relates to the delivery of what is herein defined as augmentation therapy (AT) as an intervention for sleep-disordered breathing. In general, AT involves the use of electrical stimulation to increase the stroke volume and/or ventricular pressure during one or more subsequent cardiac cycles. While AT stimulation may be of a sufficient magnitude to capture, such pulses are distinct from pacing pulses due to their timing during the refractory period. AT also includes non-excitatory pulses (i.e., insufficient magnitude to capture) that may be delivered throughout the cardiac cycle and are followed by a pacing pulse or by an intrinsic depolarization. AT may be used alone or in conjunction with other sleep-disordered breathing therapies such as atrial overdrive pacing, CPAP and the like.

In one embodiment, the present invention is an implantable medical device (IMD) for delivering therapy for sleep-disordered breathing having a detection module for determining the presence of sleep-disordered breathing. The IMD also includes a stimulation module for delivering augmentation therapy in the form of electrical stimulation to cardiac tissue when the detection module indicates a presence of sleep-disordered breathing.

In another embodiment, the present invention is an implantable medical device (IMD) for delivering therapy for sleep-disordered breathing including means for determining the presence of sleep-disordered breathing. The IMD further includes means for delivering augmentation therapy when the means for determining indicates the presence of sleep-disordered breathing.

The present invention also includes a method of utilizing an implantable medical device to provide therapy for sleep-disordered breathing. The method includes determining if sleep-disordered breathing is present and delivering augmentation therapy in the form of electrical stimulation to cardiac tissue if sleep-disordered breathing is determined to be present.

The present invention also includes a computer readable medium containing instructions that when implemented, cause an implantable medical device to perform actions to provide therapy for sleep-disordered breathing. The actions include determining if sleep-disordered breathing is present and delivering augmentation therapy in the form of electrical stimulation to cardiac tissue if sleep-disordered breathing is determined to be present.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 4A and 4B are graphical representation of physiological data indicative of respiration, heart rate, and the application of augmentation therapy.

DETAILED DESCRIPTION

Figure 1:
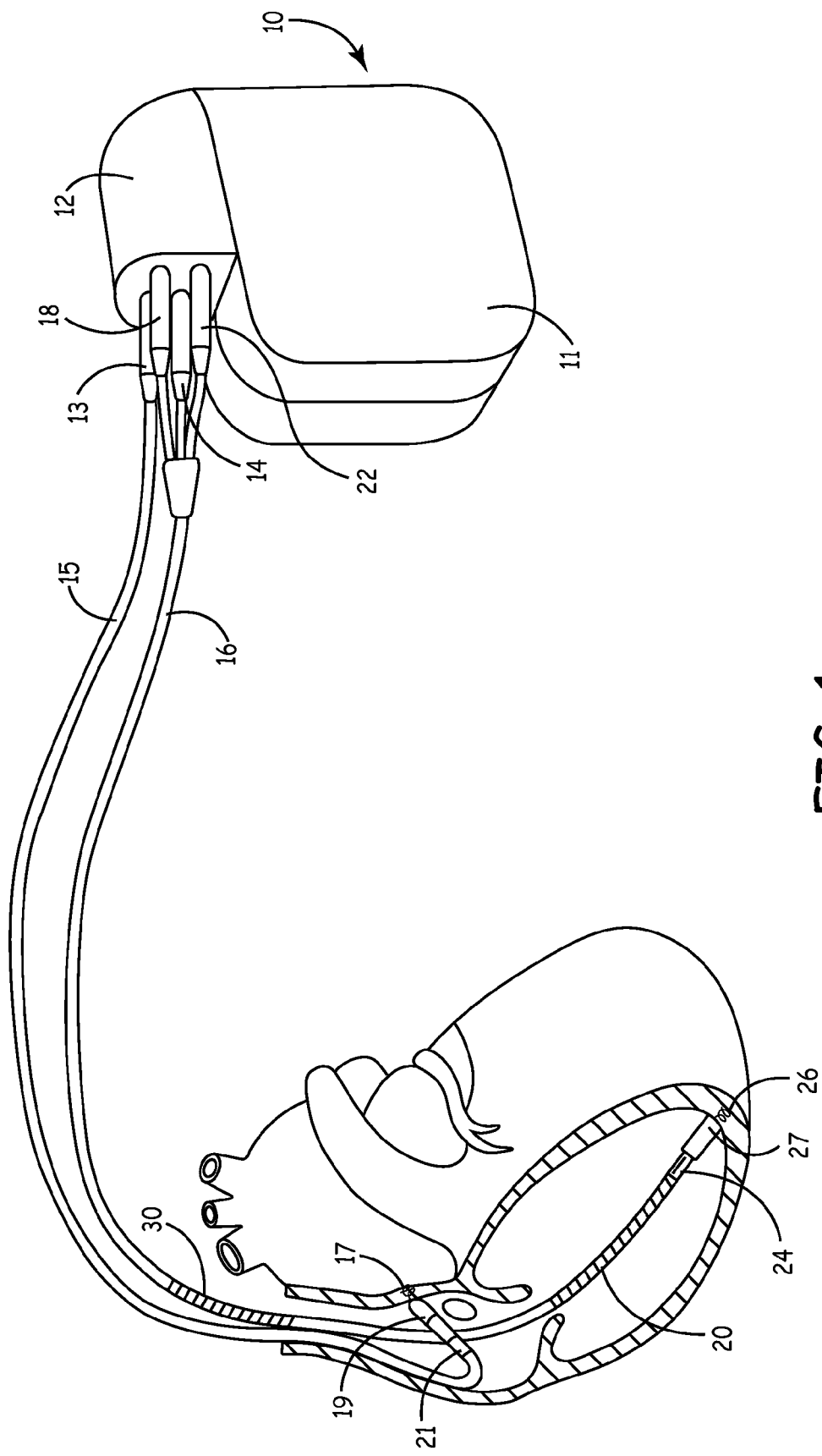
FIG. 1 is an illustration of an ICD type system according to the present invention.

Referring now to FIG. 1, there are illustrated an ICD 10 and leads 15 and 16, making up the system. ICD 10 is an implantable cardioverter defibrillator. It should be appreciated that such a device may include pacing, defibrillation, cardioversion, and/or other therapies alone or in any combination. The leads shown are illustrative, it being noted that other specific forms of leads are within the scope of this invention. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for bipolar sensing of ventricular depolarizations. While electrodes 24 and 26 may be used for bipolar pacing and sensing, electrode 26 may be used in conjunction with the surface of device casing 10, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SVC coil 30, which can be used for applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 20, 24, 26 and 30.

Atrial lead 15 as illustrated includes an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An ICD device 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
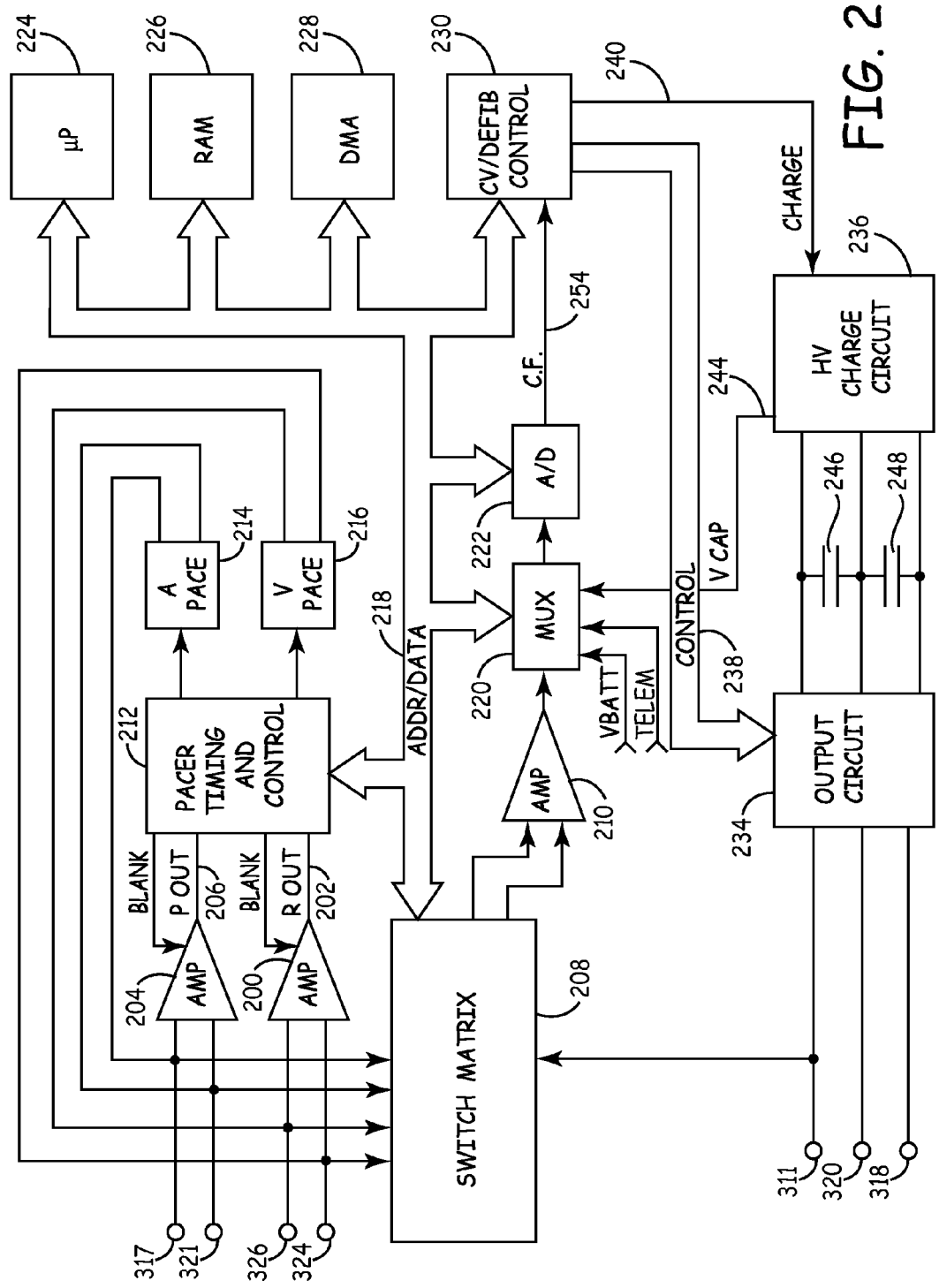
FIG. 2 is a block, functional diagram of an ICD type device adapted to carry out the features of the present invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the ICD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the ICD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available ICDs, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
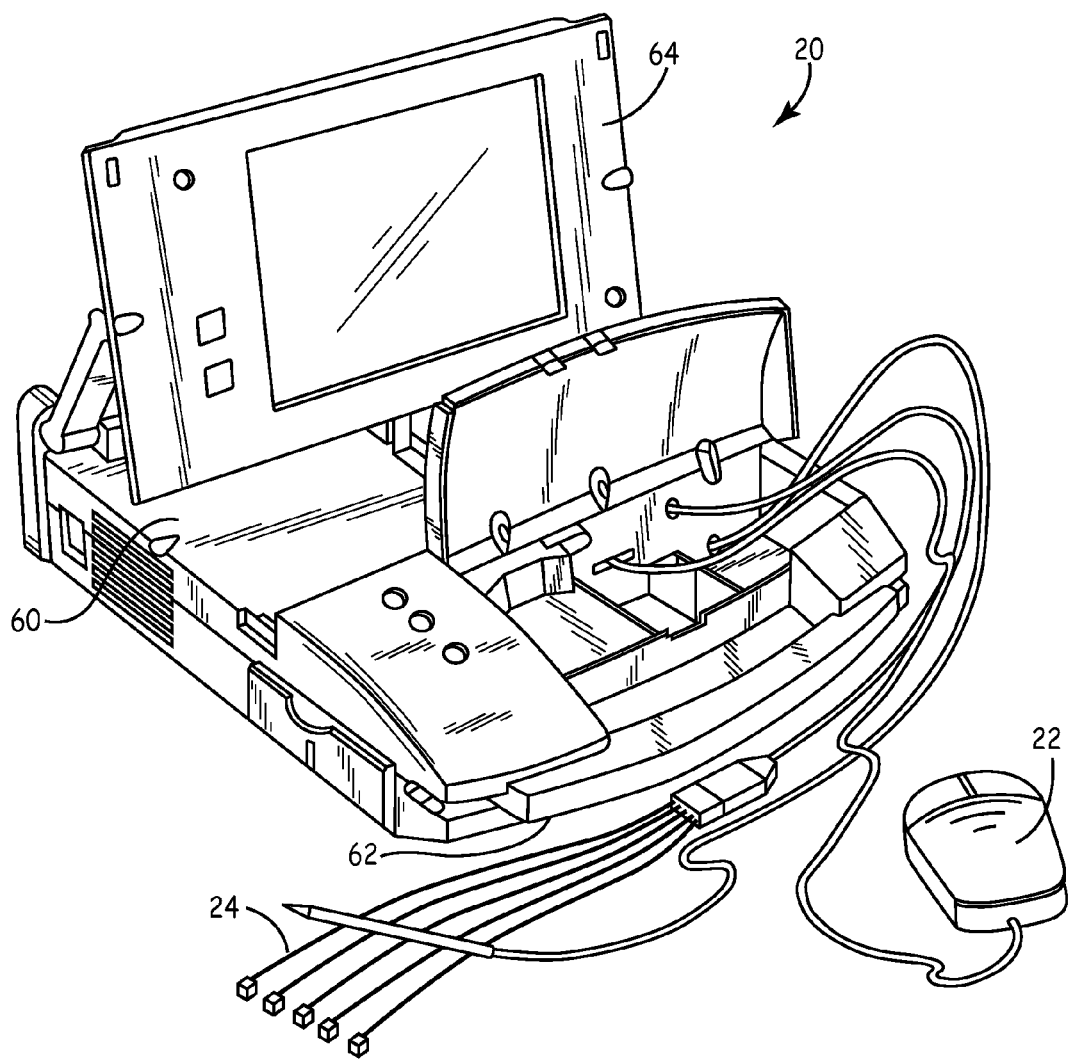
FIG. 3 is a perspective view of the external programming unit of FIG. 1.

FIG. 3 is a perspective view of programming unit program 20 in accordance with the present invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system, heart rhythm, electrical activation and a number of other parameters. Normally, programmer 20 is equipped with external ECG leads 24.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled *Portable Computer Apparatus With Articulating Display Panel*, which patent is hereby incorporated herein by reference in its entirety. The Medtronic Model 9790 programmer is the implantable device-programming unit with which the present invention may be advantageously practiced.

The above-described ICD 10 is one illustrative embodiment of an implantable medical device that can be used to deliver therapies for sleep-disordered breathing. It should be appreciated that various other devices and configurations may likewise be used including single, dual, triple and quadruple chamber pacing devices with a wide variety of lead types and structures. The use of a pacing therapy for sleep-disordered breathing may be the primary purpose of such an implantable device. Alternatively, the implantable device may deliver any number of other therapies as well. As such, the particular device chosen will be selected based on the desired therapy options.

In general, the present invention relates to the delivery of therapy in the form of electrical stimulation that increases cardiac stroke volume and/or ventricular pressure in one or more subsequent cardiac cycles, alone or in combination with other therapies, in order to provide intervention in sleep-disordered breathing. The electrical stimulation can be sub-threshold pulses or pulse-trains referred to as non-excitatory stimulation/cardiac contractility modulation (NES/CCM). NES/CCM is described, for example, in U.S. Pat. Nos. 6,233,484; 6,292,693; and 6,317,631 which are all incorporated by reference in their entirety. Alternatively, or in addition to NES/CCM, the electrical stimulation can be at or above a capture threshold. This technique is referred to as paired pacing, coupled pacing, or post-extra systolic potentiation therapy (PESP). PESP is described in U.S. Pat. No. 5,213,098, which is hereby incorporated by reference in its entirety.

NES/CCM involves the application of non-excitatory pulses and/or pulses during a refractory period, such that propagating activation potentials are not induced. In doing so, the contraction of selected segments of cardiac tissue can be increased, thus increasing the cardiac stroke volume and/or ventricular pressure. In general, with NES/CCM contractility is enhanced by action potential duration prolongation and enhanced intracellular calcium release.

PESP involves one or more premature or extrasystolic beats occurring at a time denoted the ESI (for extrasystolic interval). The extrasystole occurs before the sarcoplasmic reticulum has a chance to fully recover or become restituted and thus results in a stunted intracellular $Ca^{++}$ transient that is both early and associated with little developed force. At the same time, the calcium entering the cell across the cell membrane delivers a relatively normal amount of $Ca^{++}$. The result is that on the following beat, delivered at a time called the post extrasystolic interval or PESI, the sarcoplasmic reticulum's release of $Ca^{++}$ is much greater or potentiated. The magnitude of this potentiation increases with the degree of prematurity of the extrasystole, until a minimal ESI is reached which fails to lead to a depolarization or capture. The ventricular extrasystole may result in the failed conduction of the subsequent atrial depolarization, depending on the intrinsic rate and AV conduction. This can lead to a rate halving or slowing effect where the effective mechanical rate becomes one half the atrial rate.

Thus, PESP involves the delivery of a second or paired pulse during the refractory period and timed from either a paced pulse or a sensed intrinsic depolarization. By potentiating the cardiac tissue in this manner, the subsequent full contraction of the ventricles occurs with greater force and thereby increases stroke volume and/or ventricular pressure. The effect of such potentiation is generally carried forward for the next several beats with decreasing effects until a return to normal stroke volume occurs. Thus, PESP can be delivered on every beat to maximize potentiation or intermittently, wherein increased stroke volume is achieved for a number of beats after the therapy is delivered. As mentioned, with PESP the ventricular rate may be halved with respect to the atrial rate. Thus, though PESP may be delivered for every beat, the net cardiac rate is decreased by half, with a constant atrial rate.

These therapies, NES/CCM, PESP, and others are collectively referred to herein as augmentation therapies (AT). In general, AT involves the use of electrical stimulation to increase the stroke volume and/or ventricular pressure of one or more subsequent cardiac cycles. While AT stimulation may be above capture level, such pulses are distinct from pacing pulses due to their timing during the refractory period. Non-excitatory pulses for AT (i.e., below capture level stimulation) may be delivered throughout the cardiac cycle and are followed by a pacing pulse or by an intrinsic depolarization.

FIG. 4A is graphical representation of a patient's respiration and heart rate during certain periods involving apnea and hyperventilation. At point A, the patient is having an apnea. That is, there is a cessation of breathing (regardless of whether it is central or obstructive in origin). At the same time, the patient's heart rate is illustrated as decreasing from a previous cycle of what is currently being described. If the previous respiration parameters had been normal, the heart rate at A would be normal (i.e., not elevated). Thus, at least initially during the apnea heart rate generally does not increase.

As the apnea continues, the oxygen ($pO_2$) in the blood is decreasing from the lack of respiration. In addition, carbon dioxide in the blood ($pCO_2$) is increasing. At point B, the $pCO_2$ reaches a level above a threshold value sufficient to trigger breathing. As a result, the patient generally resumes respiration with a gasp. However, as the $pCO_2$ levels were elevated the natural reaction is to breathe deeper and faster, and hence hyperventilate. Hyperventilation is illustrated as beginning to occur at some point after B to a maximum at C. At the same time, the heart rate is elevating, delivering oxygen rich blood throughout the body. Thus, $pCO_2$ levels drop but often drop well below the threshold for breathing because of the hyperventilation and elevated heart rate. As the body senses the lower $pCO_2$ levels respiration slows and the heart rate steadies and then lowers, from C to D. Since the $pCO_2$ level is below threshold, respiration slows to the point of apnea again at E and the cycle repeats. That is, for central sleep apnea, the brain fails to trigger respiration, most likely due to the lowered $pCO_2$ levels. For obstructive sleep apnea, the return to normal levels of $pCO_2$ allows the patient to relax and fall back to sleep, which in turn allows the mechanical obstruction to recur. For example, the relaxed throat tissue may collapse and seal off the airway. Of course, FIG. 4A is meant to illustrate the apnea cycles and does not include periods of normal respiration, which would also likely be present.

The present invention provides for the delivery of augmentation therapies to interrupt or intervene in the SDB cycle. When augmentation therapy is delivered, stroke volume and/or ventricular pressure are increased. Thus, increased levels of oxygen are delivered quickly and forcefully through blood flow. That is, without AT, the body must sense the elevated levels of $pCO_2$, then begin to respond by increasing heart rate gradually. This takes time and tends to shift the levels of saturated oxygen and carbon dioxide too far in the other direction. The use of AT prevents the dramatic shifts above and below threshold values for the sensed pCO$_2$ and effectively stabilizes the pCO2 and PO$_2$. As such, central sleep apnea is greatly reduced or eliminated. Obstructive sleep apnea is reduced or eliminated as well. As previously mentioned, some cases of obstructive sleep apnea may be triggered by central sleep apnea. Thus, the elimination of central sleep apnea may contribute to reduction in the frequency of obstructive sleep apnea. In addition, for true obstructive sleep apnea, AT therapy will reduce or eliminate the occurrence of apneas by increasing autonomic tone.

The timing and delivery of AT can be varied. FIGS. 4A and 4B illustrate initiating AT when hyperventilation is detected. Similarly, AT could be initiated when an elevated heart rate is detected. As illustrated, AT is turned on for a period of time, then turned off when normal respiration would occur with a normal stroke volume. The desired result, as illustrated in FIG. 4B is that respiration and/or heart rate are maintained at a relatively even rate.

As illustrated, AT is delivered when a certain condition is detected, e.g., heart rate, respiration, pCO$_2$ levels, pO$_2$ levels, muscle tone, or any other parameter indicative of the onset or occurrence of apnea. In addition, AT is delivered only during sleep, which may be detected, programmed, or based on time. In one embodiment, AT is cyclically delivered. In another embodiment, AT, once initiated, is delivered continuously throughout the sleep period. In one embodiment, AT is initiated only after an apnea or the onset of apnea is detected. In another embodiment, AT is delivered whenever the patient is in a sleep state.

The rate at which AT is delivered will depend upon the specific therapy options selected. AT may be delivered for every cardiac cycle, or on every $n^{th}$ cycle (e.g., every other cycle, every $3^{rd}$, $4^{th}$, etc.) The rate will depend on the therapy or combination of therapies chosen and the physiological requirements of the patient. In one embodiment, the apnea cycle previously described is monitored and timed. Subsequent delivery of AT is based on that time. Furthermore, in another embodiment, AT may be delivered somewhat predictively at every $n^{th}$ respiration or cardiac cycle, wherein n represents the average number of cycles between apneas. Alternatively, AT would be delivered at every n–y (n minus y) respiration cycle, wherein y is a predetermined number selected so that AT is delivered before the onset of apnea.

Figure 5:
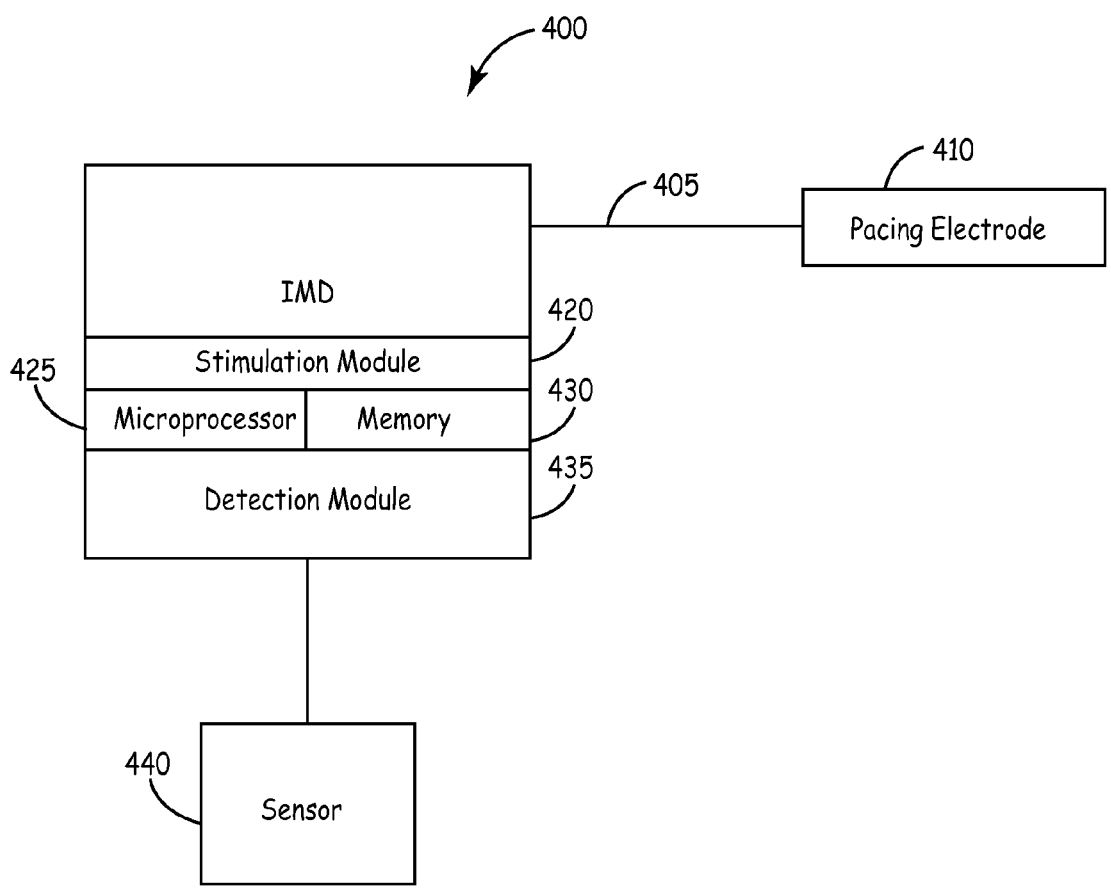
FIG. 5 is a schematic diagram of an implantable medical device useful for delivering augmentation therapies.

FIG. 5 is a schematic illustration of an implantable medical device (IMD) 400 useful for delivering AT. In one embodiment, IMD 400 is equivalent to ICD 10 previously described. IMD 400 may include a wide variety of functions such as cardioversion, defibrillation, drug delivery, sensing, monitoring, and recording. In order to provide AT, IMD 400 delivers electrical stimulation to cardiac tissue at appropriate points in the cardiac cycle. This is most commonly accomplished via a pacing lead 405 having a pacing electrode 410 that is proximate or in contact with cardiac tissue within a ventricle. Of course, additional leads could be provided for other purposes including dual, triple, and quadruples sensing, pacing and defibrillation.

IMD 400 includes a stimulation module for delivering the appropriate electrical stimulation at the appropriate time, including AT as well as traditional pacing (if provided). These functions could be carried out by separate components as well. The timing is based on data sensed through the lead 405 relative to the cardiac cycle and data acquired from a microprocessor 425 relating to traditional pacing (if applicable). A memory 430 is provided for storing algorithms for use with the microprocessor 425 for delivering the appropriate augmentation therapy. If AT is delivered based on a sensed parameter (e.g., respiration), the IMD 400 also includes a detection module 435 and a sensor 440 for gathering the requisite data and providing those parameters to the microprocessor 425 for the appropriate delivery of AT.

If AT is delivered based on heart rate, lead 405 would provide an adequate sensor. Other leads used with the ICD 10 could likewise provide appropriate sensor data. Alternatively, various other sensors 440 would be implanted or coupled externally to the patient and provide data to the detection module 435, either through a hard-wired connection (e.g., a lead) or via telemetry or some other wireless communication protocol. Sensor 440 could be an impedance based sensor for monitoring minute ventilation, a mechanical or temperature sensor for monitoring air flow (breathing) or chest movement, an oxygen sensor, a carbon dioxide sensor, a chemical sensor for monitoring a derivative indicative of oxygen or carbon dioxide, a pressure sensor for monitoring blood pressure either internal or external to the heart or sensing air flow (breathing), a microphone for monitoring breath sounds, one or more neural sensors for monitoring brain activity, or any other sensor capable of monitoring a parameter indicative or predictive of the occurrence of apnea or the onset of apnea. IMD 400 may also be used in combination with an external device, such as a CPAP machine. Thus, IMD 400 may communicate with such a device, thereby receiving data and/or sending data relating to sensed parameters and/or therapy delivery (e.g., CPAP pressure, rate, effectiveness, etc.).

As previously indicated, the delivery of AT may be a primary therapy wherein IMD 400 is a dedicated device for that purpose. Alternatively, IMD 400 provides various other therapies (e.g., pacing, defibrillation, monitoring, drug delivery, etc.) and AT is simply an additional therapy choice provided. In addition, AT is a therapy option that can be programmed into existing and implanted devices.

Figure 6:
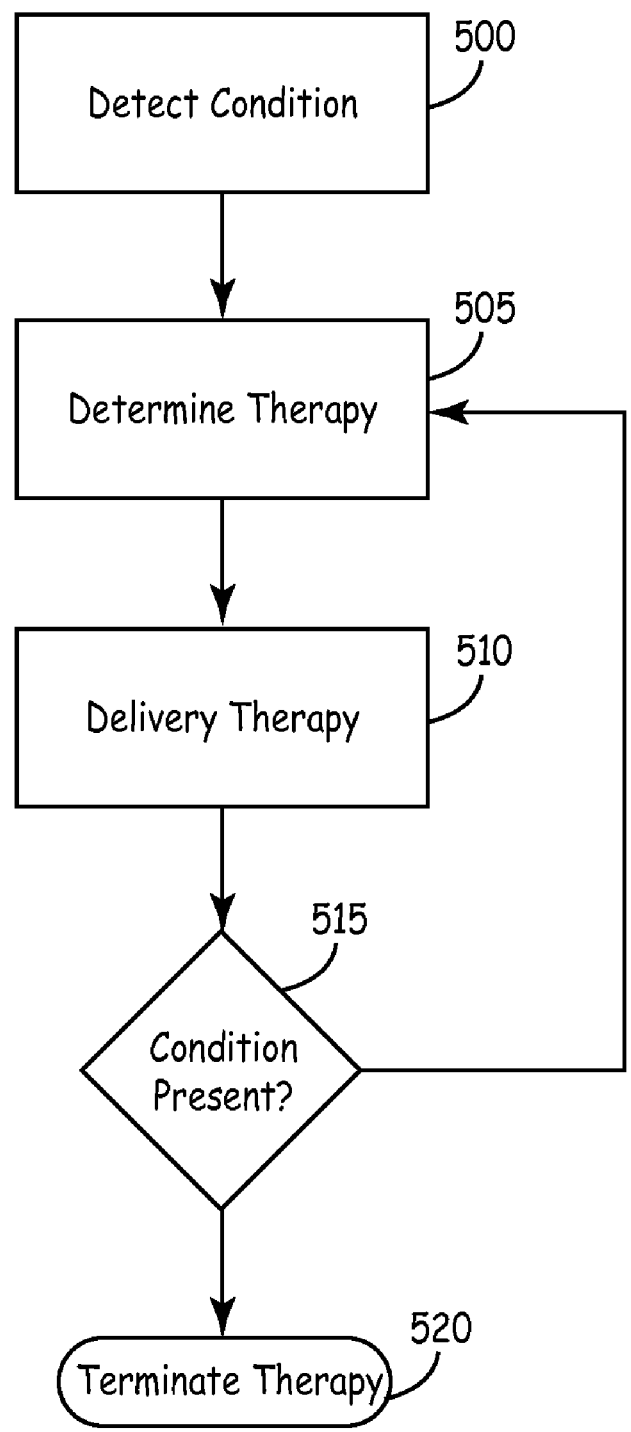
FIG. 6 is a flowchart illustrating a process of delivering augmentation therapy.

FIG. 6 is a flowchart illustrating the use of IMD 400 to deliver AT as an intervention for SDB. At step 500, the condition is detected. This can either be a general or a specific parameter indication. That is, the physician may monitor the patient (e.g., a sleep study) and determine that apnea is present. Based on that, a device may be implanted or programmed to thereafter deliver AT without subsequent detection of apnea related parameters. IMD 400 will determine when AT should be delivered based on a sleep state that can either be detected (e.g., heart rate, body movement, brain activity, respiration, etc.) or based on time (e.g., the patient is presumed asleep between 12:00 a.m. and 6:00 a.m.).

Alternatively, at step 500, the IMD 400 detects the appropriate condition, such as an apnea that toggles AT to an on state. This initial detection of an apnea would inhibit the delivery of AT when the patient is sleeping and breathing normally. For example, some patients may only suffer sporadically from sleep apnea. Once so toggled, the IMD 400 can deliver AT either based on programmed parameters (e.g., every $n^{th}$ cardiac cycle or every $n^{th}$ respiration), based on specific detected events (e.g., elevated heart rate, hyperventilation, apnea), or a combination of the two. That is, once a toggling event is detected, a parameter is measured by which subsequent delivery of AT is applied. For example, respiration cycles or time during an apnea cycle may be monitored to determine an average. AT is then subsequently delivered for that duration.

Step 500 is ultimately a determination to deliver AT. At 505, the specific therapy is chosen. This can be a preprogrammed function (e.g., AT will always be PESP) or the IMD 400 can select the appropriate AT as well as other apnea therapies to be used in various combinations.

At step 510, the appropriate therapy is delivered and at 515 there is a determination made if the condition is still present. The condition detected, in one embodiment, is broad. That is, the condition is a sleep state and the process is returned to step 505 so long as the patient is in the sleep state. Alternatively, the condition is apnea specific. If the monitored parameters are normal, AT is ceased until apnea indicative parameters are subsequently detected and the process repeated. The therapy delivery step 510 in one embodiment applies to a single delivery of AT. Alternatively, AT may be delivered for a predetermined period of time, predetermined number of cardiac cycles, predetermined number of respirations, or as previously indicated, throughout the patient's sleep state.

In determining the appropriate therapy at step 505 there are many options available. It should be appreciated that these options could be selected in advance by the programming physician, determined and set by the IMD 400 based on detected parameters, or varied by the IMD 400 based on detected conditions. In addition, the options may be provided in an incremental format. That is, first try therapy A, if unsuccessful, then try therapy B, and so on.

The present invention provides for the use of AT, thus AT is one option selectable at step 505. AT includes among other things, NES/CCM and PESP. NES/CCM generally means that that sub-threshold stimulation is delivered. However, what that below threshold level is can be selected to provide the most effective apnea intervention. Similarly, PESP includes above-threshold stimulation; however, the amplitude and timing within the cardiac cycle and the frequency of the therapy (e.g., every cardiac cycle, every $n^{th}$ cardiac cycle, etc.) are again variable and are selected to provide the most effective apnea intervention. PESP and NES/CCM can be delivered in combination as a course of AT. Thus, determining which therapy to deliver at step 505, means determining which form of AT to deliver along with the timing and stimulation levels.

In addition to delivering AT, other apnea therapies may be delivered in combination with or prior to delivering AT. For example, atrial overdrive pacing (AOP) is a selectable option. In one embodiment, AOP is delivered and then, if unsuccessful, AT is delivered. In another embodiment, both AOP and AT are delivered simultaneously.

AOP can be combined with PESP alone, with NES/CCM alone, both PESP and NES/CCM, or with other forms of AT. The combination of AOP and NES/CCM will tend to increase overall cardiac output due to the rate increase as well as increasing stroke volume and/or ventricular pressure.

Atrial pacing combined with PESP presents many variables that can be adjusted to produce desirable effects. For example, PESP has a rate-halving effect. That is, when PESP is applied to every permissible cardiac cycle then every other conducted atrial depolarization fails to lead to ventricular depolarization. Therefore, if atrial pacing is delivered to produce an atrial rate that is twice the actually desired rate then the effective ventricular rate is the desired rate. The use of an elevated atrial rate to produce a desired ventricular rate when PESP is applied is referred to as atrial coordinated pacing (ACP). As previously mentioned, PESP increases stroke volume and/or ventricular pressure but due to the rate halving does not generally increase overall cardiac output. When ACP and PESP are combined, overall cardiac output is increased along with the increase in stroke volume and/or the increase in ventricular pressure. Of course, various atrial rates can be achieved, as can various ratios of applying PESP (e.g., every $n^{th}$ cycle, etc.) so that the most beneficial and least interruptive therapy is achieved.

In one embodiment, AOP, PESP and NES/CCM are all combined simultaneously. Thus, maximum control over cardiac rate, cardiac output, stroke volume, and ventricular pressure is facilitated. The various parameters can be selected to deliver the therapy having the greatest success. Of course, various other factors should be considered when setting the parameters, not the least of which is power consumption. Combining all of these therapies together, particularly for extended periods of time will draw added amounts of power. Thus, effects such as the sustained effect of PESP for subsequent cardiac cycles should be considered when programming the therapy parameters.

Figure 7:
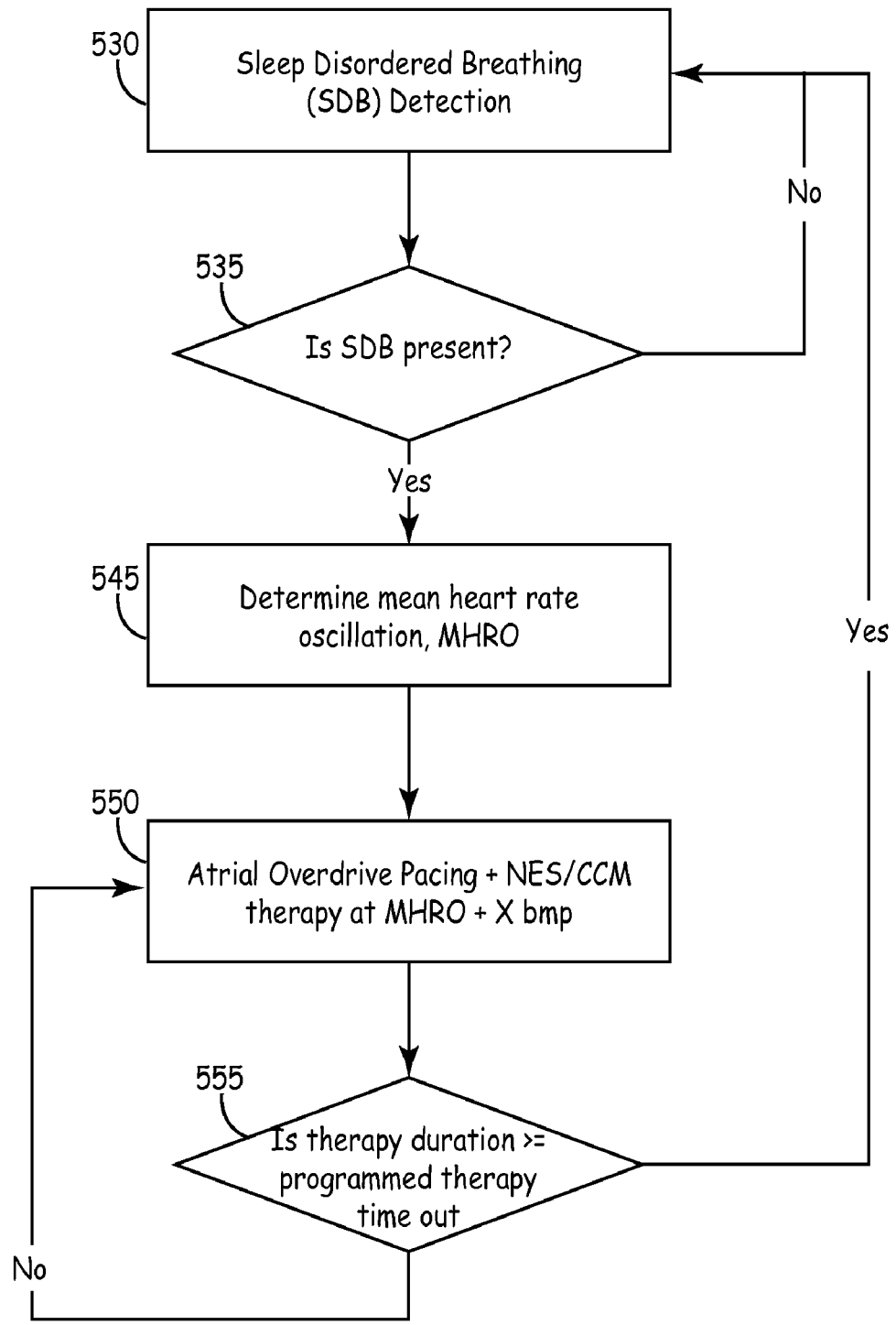
FIG. 7 is a flowchart illustrating a process of detecting SDB and delivering augmentation therapy.

FIG. 7 is a flowchart illustrating one embodiment of utilizing AT for intervention in sleep-disordered breathing. IMD 400 implements (530) a sleep-disordered breathing (SDB) detection algorithm and determines (535) whether SDB is present. If SDB is not present, the algorithm loops back to the detection (530) phases and continues to monitor for SDB.

If SDB is present, then IMD 400 monitors the patient's heart rate and determines (545) the mean heart rate oscillation (MHRO). MHRO is a quantifiable variant that is indicative of the types of heart rate fluctuations illustrated in FIG. 4A. Augmentation therapy is then delivered (550). In this embodiment, the augmentation therapy is NES/CCM and is utilized in conjunction with AOP. The rate for the AOP is determined by adding a predetermined quantity (X BPM) to the MHRO. X may vary from, for example, a few beats per minute, 10 beats per minutes, 30 beats per minute, or any rate from 1 to a maximum safe rate. In one embodiment, X is predetermined and fixed during programming. Alternatively, IMD 400 determines the appropriate value for X. In another embodiment, IMD 400 increases the value of X and monitors the patient to determine an optimal value.

Thus, AT and AOP are delivered (550) for some period of time. That time is monitored and the therapy is delivered (550) throughout. Once a programmed therapy time out duration has been exceeded (555), the process is restarted to monitor for SDB (530).

While one particular embodiment has been described, numerous variations are within the scope of the present invention. For example, the presence of SDB can be presumed (e.g., assume it is present whenever the patient is asleep). Thus, therapy can be delivered without subsequent detection. Alternatively, once therapy is initially delivered, the therapy can be continuously delivered or delivered on an interactive basis without subsequent detection.

Figure 8:
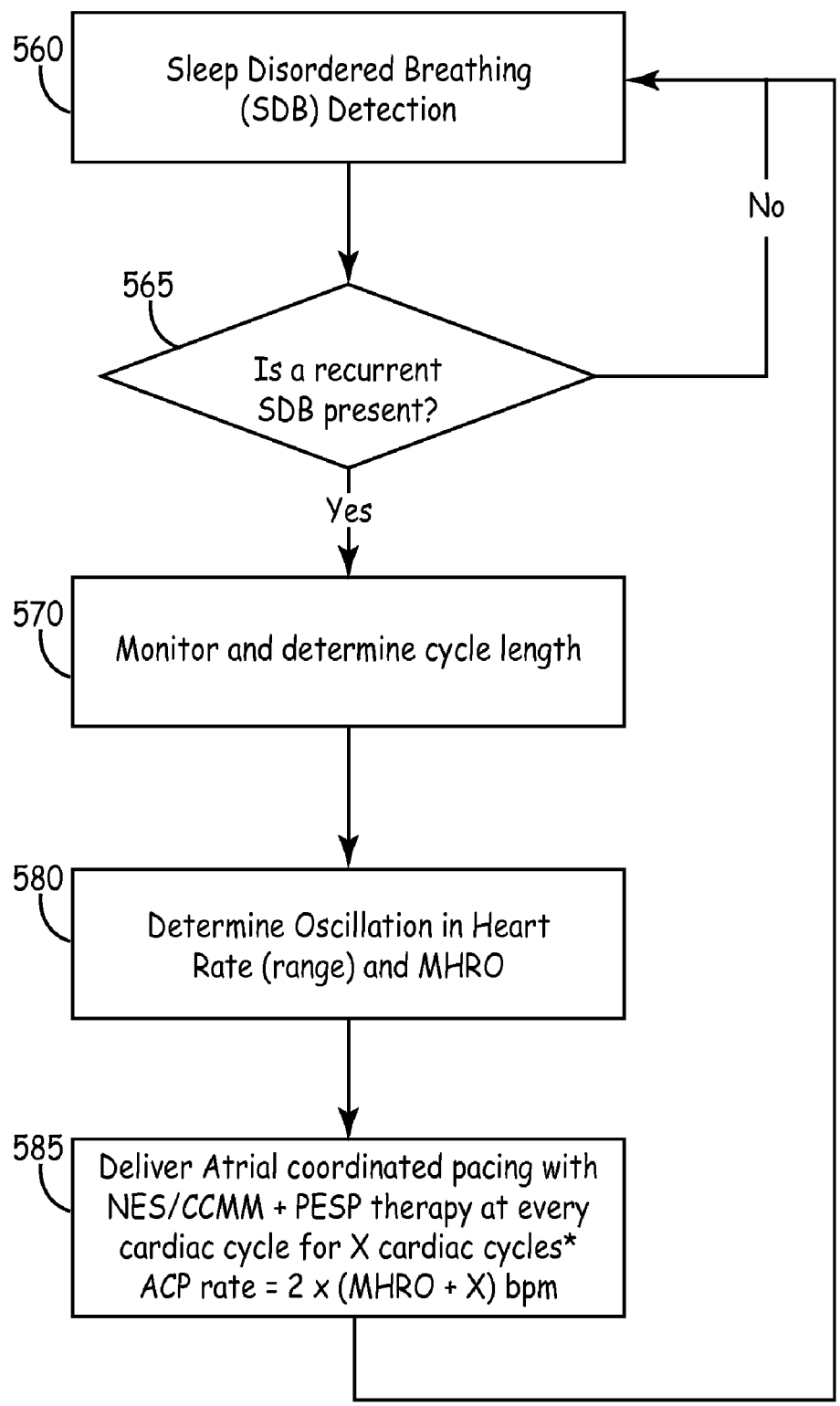
FIG. 8 is a flowchart illustrating another process of detecting SDB and delivering augmentation therapy.

FIG. 8 is a flowchart that illustrates another embodiment of utilizing AT for SDB intervention. IMD 400 detects (560) one or more parameters indicative of SDB. Based on such detection, IMD 400 determines if SDB is present (565) and recurrent. If SDB is not detected, then IMD continues to monitor (560).

If SDB is detected (565), then IMD 400 monitors (570) the SDB and determines the cycle length of the SDB episodes. The parameters used for the measured cycle length will vary upon desired usage. For example, parameters such as duration of apnea, duration of hyperventilation, intervals between SDB events, or other relevant parameters may be used.

IMD 400 monitors the heart rate and determines (580) the MHRO as well as the overall range of heart rate oscillations. AT is delivered (585) along with Atrial Coordinated Pacing (ACP). In this embodiment, AT consists of NES/CCM in combination with PESP. AT is delivered during every cardiac cycle and the combination of AT and ACP is delivered for X number of cycles. The number of cycles that therapy is delivered (X) will be determined based on the cycle length previously measured (570). That is, one goal of the therapy is to even out oscillations in heart rate and/or breathing rate, or tidal volume; thus, the therapy is delivered in and for intervals appropriate to achieve this effect.

In this embodiment, the combination of delivered therapies includes an AOP component. AOP as a therapy is meant to increase the overall cardiac rate through atrial pacing. That is, there is a presumed 1:1 conduction to the ventricles so that the ventricular rate corresponds to the atrial rate. ACP, which also increases the atrial rate, is used with the understanding that PESP will reduce the ventricular rate to something less than the paced atrial rate. Therefore, in order to deliver AOP as a therapy, the rate of ACP must be increased by an appropriate amount so that the ventricular rate is that of the desired AOP rate. In one embodiment, the ACP rate used when AOP is included is twice the measured MHRO plus a variable Y. Y is the AOP component or offset previously discussed and is generally on the order of a few beats per minute, 10 beats per minute, 30 beats per minute, etc. Without the application of PESP, atrial pacing at the MHRO plus Y rate would achieve AOP, as described in FIG. 7. However, in the present embodiment, PESP will reduce the ventricular rate to one half of the paced atrial rate (since PESP is being delivered for every cardiac cycle). Thus, doubling the MHRO plus Y rate effectively achieves an elevated ventricular rate. Of course, in other embodiments, ACP could be applied without utilizing an AOP component, thus Y would be zero. In other embodiments, AT including PESP could be delivered without ACP if there was a desire to reduce the ventricular rate from the intrinsic rate.

Figure 9:
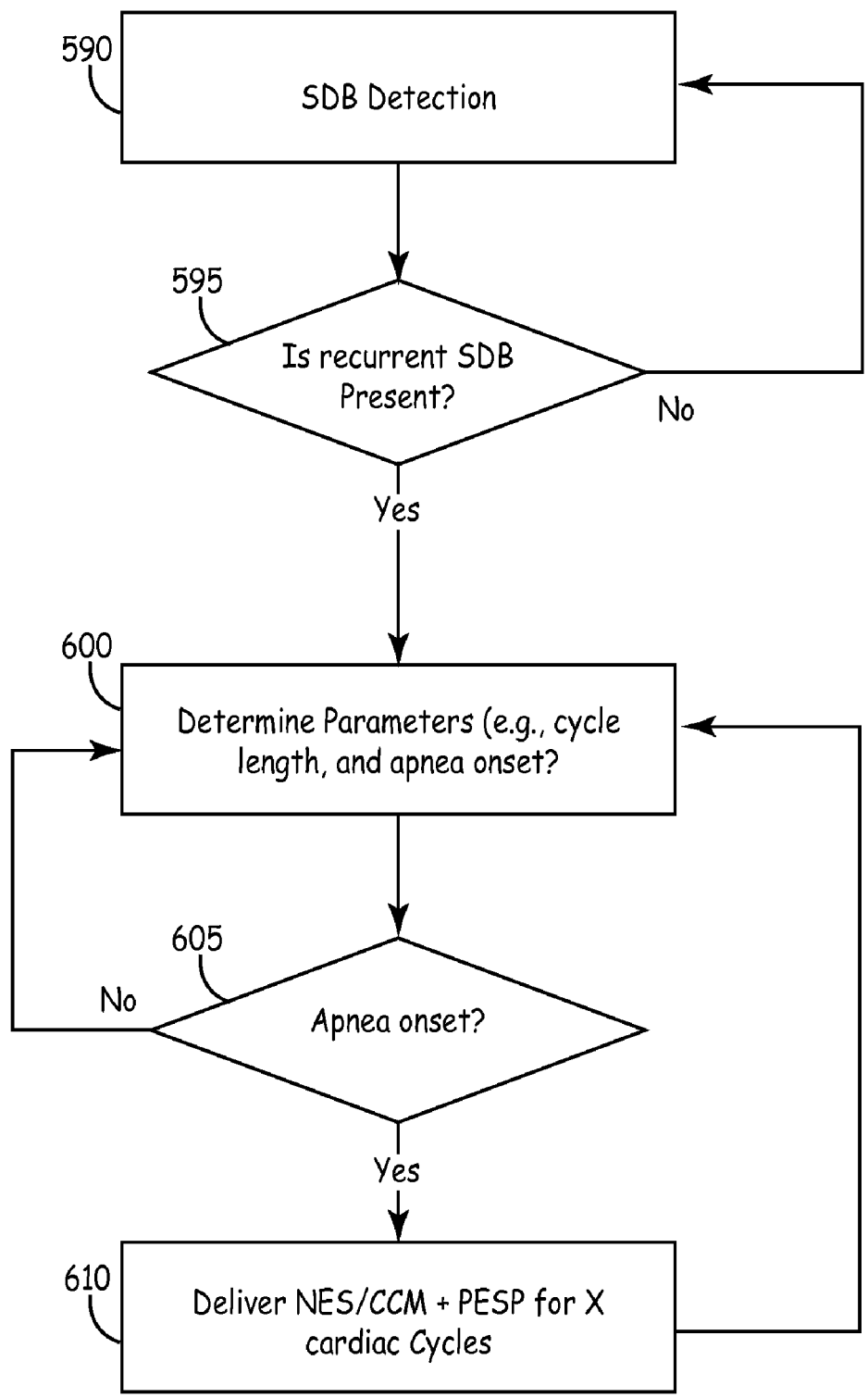
FIG. 9 is a flowchart illustrating another process of detecting SDB and delivering augmentation therapy.

FIG. 9 is a flowchart illustrating another embodiment of delivering AT for SDB intervention. IMD 400 determines (590) whether SDB is present and whether SDB is recurrent (595). If recurrent SDB is not detected, IMD 400 continues to monitor (590) for the condition. If recurrent SDB is present, then IMD 400 determines (600) certain parameters relating to the SDB. For example, such parameters include cycle length, hypopnea onset/duration, apnea onset/duration, heart rate or other relevant parameters.

When IMD 400 has gathered sufficient data (600) through one or more episodes of SDB, then IMD 400 monitors for the next onset of apnea (605). For example, referring to FIG. 4A, onset may be indicated by increased respiration, hyperventilation, hypopnea, heart rate or various other parameters. Onset is meant to indicate that apnea will occur or is likely to occur in some predetermined period of time, based on detected parameters.

If IMD 400 determines the onset of apnea (605), then IMD 400 delivers the augmentation therapy for X number of cardiac cycles. X is either preprogrammed or determined by IMD 400 based upon factors such as the measured cycle length of the SDB. By delivering AT prior to apnea, the SDB pattern is interrupted, apnea does not occur, and the patient maintains more even respiration and cardiac rates. In the present embodiment, AT includes the delivery of NES/CCM and PESP. In an alternative embodiment, apnea detection (605) indicates that an apnea is occurring. Therapy delivery can then begin immediately and/or in a predetermined period of time based upon the measured cycle length of previous SDB episodes so that subsequent SDB episodes are interrupted.

Figure 10:
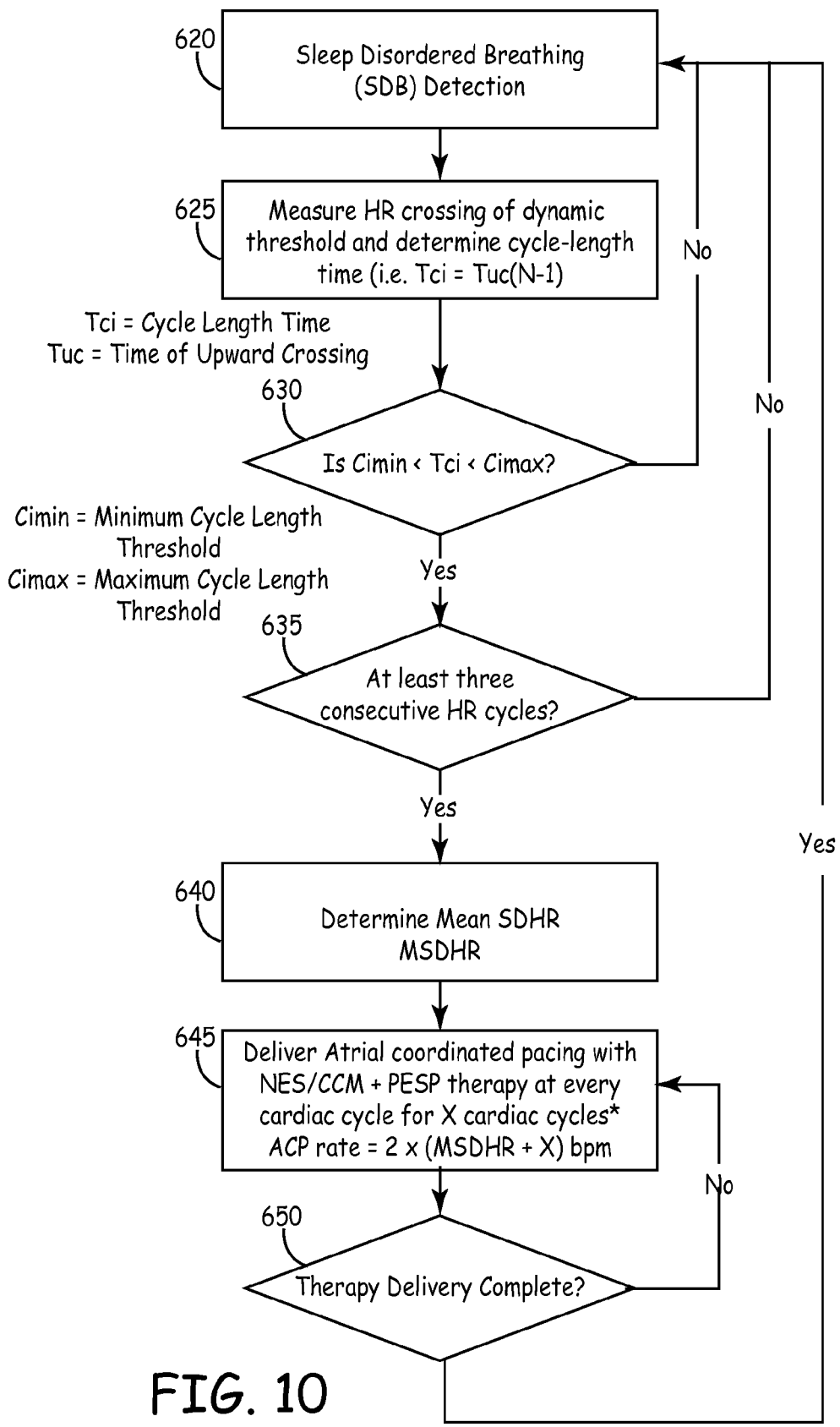
FIG. 10 is a flowchart illustrating another process of detecting SDB and delivering augmentation therapy.

FIG. 10 is a flowchart illustrating the detection of SDB and the delivery of AT. IMD 400 monitors for and detects (620) SDB. In this embodiment, an algorithm is provided for SDB determination based on heart rate monitoring. A dynamic threshold is programmed into or determined by IMD 400. The dynamic threshold is a heart rate that is indicative of SDB or the onset of SDB. As SDB is often recurrent, IMD 400 monitors the heart rate and determines (625) when (Tuc) the heart rate increases above the dynamic threshold. With a subsequent SDB episode, IMD 400 again monitors the time at which the heart rate increases above the dynamic threshold. These time data points ($TuC_{(N)}$ and $TuC_{(N-1)}$) are subtracted resulting in a cycle time length (Tcl). That is, the time between subsequent episodes of SDB, as indicated by an elevated heart rate.

This time data point (Tcl) is then evaluated (630) to determine if it is between a minimum and maximum threshold (Clmin–Clmax). If the measured Tcl is not within this range, it is ignored and IMD 400 continues to monitor (620). For example, if the cycle length is too short, it may indicate that other conditions are occuring; thus, the measurements should not be used to establish average cycle times. Similarly, if the cycle time is too long, then the SDB may be more sporadic and should not be used to establish a pattern.

If the determined cycle time falls within the range for consideration (630), then IMD 400 determines if a sufficient number of consecutive cycles have occurred (635). For example, in the present embodiment, three consecutive cycles wherein Tcl falls within the range are required. The number of required consecutive cycles can be programmed to give a desired level of reliability. If the current determined Tcl is not the third, then IMD continues to monitor (620). If the determined Tcl is the third consecutive cycle falling within the range, then IMD 400 determines (640) the mean sleep-disordered heart rate (MSDHR) by averaging the three determined cycle times. Alternatively, X of Y type of cluster detection can be used. For example, if three valid cycles are present in most recent 5 cycles, then the condition is satisfied, rather than requiring a predetermined number of consecutive cycles.

IMD 400 will then deliver the augmentation therapy. In this embodiment, AT includes PESP and NES/CCM, along with ACP (with an AOP offset), similar to that previously described. The ACP rate is twice the MSDHR plus the AOP offset (Y). Thus, the therapy delivered (645) maintains the ventricular rate above the MSDHR and delivers AT. The therapy is delivered for a predetermined number of cardiac cycles (X), with X being based on the measured cycle length. Once again, the goal is to even out the variations in breathing and heart rate so the therapy is delivered cyclically to interrupt the occurrence of SDB episodes. Therapy is delivered for those X cycles (650) and then the process is repeated (620) to continuously update the MSDHR. Alternatively, once calculated the therapy is delivered cyclically or based on the detected onset of an SDB episode. The MSDHR can be calculated once per patient, once per sleep cycle, on a timed basis (e.g., hourly), for every delivery of therapy, or at any interval desired.

Various illustrative embodiments having been shown and described. It should be appreciated that various options and selections are presented for each embodiment. These options and selections are combinable in any number of ways and combinations are not limited to the specific embodiments described herein. For example, the present invention includes various ways to identify, monitor, measure and/or anticipate SDB. There are a variety of ways of determining when and for how long SDB therapy will be applied. Similarly, there are various forms and combinations of AT. In addition, there are various other therapies that are used in combination with AT, such as AOP and ACP. All such combinations are considered within the scope of the present invention.

Although the present invention has been described with reference to preferred embodiments, persons skilled in the art will recognize that changes may be made in form and detail without departing from the spirit and scope of the invention.

We claim:

1. An implantable medical device (IMD) for delivery therapy for sleep-disordered breathing comprising:
    means for determining the presence of sleep-disordered breathing;
    means for delivering augmentation therapy when the means for determining indicates the presence of sleep-disordered breathing;
    means for providing atrial pacing in combination with the augmentation therapy; means for determining a cycle length of a sleep-disordered breathing episode, wherein the means for delivering augmentation therapy deliver the therapy for a period of time based on the determined cycle length and
    means for calculating a mean heart rate, wherein the means for providing atrial pacing pace the atria at an atrial rate that is a multiple of a desired ventricular rate and the desired ventricular rate is determined based on the mean heart rate.

2. The IMD of claim 1, further comprising:
    means for identifying the onset of an episode of sleep-disordered breathing; and
    means for causing the means for delivering to deliver the augmentation therapy prior to the onset of the episode.

3. The IMD of claim 1, further comprising:
    means for calculating a mean heart rate, wherein the means for providing atrial pacing pace the atria at an atrial rate equal to the mean heart rate plus a predetermined value to achieve atrial overdrive pacing.

4. The IMD of claim 1, wherein the multiple is two (2).

5. The IMD of claim 1, wherein the desired ventricular rate is the mean heart rate.

6. The IMD of claim 1, wherein the desired ventricular rate is the mean heart rate plus an integer value, the integer value defining an atrial overdrive pacing offset.

7. The IMD of claim 6, wherein the augmentation therapy includes post-extra systolic potentiation having a ventricular rate reducing effect so that the desired ventricular rate is effectuated when the means for providing atrial pacing pace the atria at the atrial rate.

8. The IMD of claim 1, further comprising:
    means for determining a cycle length of a sleep-disordered breathing episode, wherein the means for delivering augmentation therapy deliver the therapy at a time prior to an onset of sleep-disordered breathing wherein the time is determined by the measured cycle length.

9. The IMD of claim 1, further comprising:
    means for monitoring a heart rate and determining if the heart rate increases over a threshold value;
    means for determining an average sleep disorder heart rate based on the heart rates from the means for monitoring; and
    means for causing an effective ventricular rate that is greater than the average sleep disorder heart rate when augmentation therapy is delivered.

10. The IMD of claim 1, wherein the augmentation therapy is non-excitatory stimulation cardiac contractility modulation (NES/CCM).

11. The IMD of claim 10, wherein the augmentation therapy is delivered along with atrial overdrive pacing (AOP).

12. The IMD of claim 1, wherein the augmentation therapy is post-extra systolic potentiation (PESP).

13. The IMD of claim 12, wherein the augmentation therapy is delivered along with atrial coordinated pacing (ACP).

14. The IMD of claim 13, wherein the ACP includes an AOP component.

15. The IMD of claim 1, wherein the augmentation therapy includes NES/CCM and PESP.

16. The IMD of claim 15, wherein the augmentation therapy is delivered along with ACP.

17. The IMD of claim 16, wherein the ACP includes an AOP component.

18. The IMD of claim 1, further comprising means for sensing a physical parameter indicative of the onset of sleep-disordered breathing.

19. The IMD of claim 18, wherein the physical parameter is chosen from the following group: respiration rate, minute ventilation, heart rate, neural activity, apnea, hypopnea, hyperventilation, breath sounds, temperature, blood pressure, chest movement, impedance, saturated carbon dioxide, and saturated oxygen.

20. A method of utilizing an implantable medical device to provide therapy for sleep-disordered breathing, comprising:
    determining if sleep-disordered breathing is present;
    delivering augmentation therapy in the form of electrical stimulation to cardiac tissue if sleep-disordered breathing is determined to be present;
    determining a cycle length for a sleep-disordered breathing episode; and
    delivering the augmentation therapy for X number of cardiac cycles, wherein X is selected based on the determined cycle length, wherein the cycle length is an averaged value of multiple sleep-disordered breathing episodes.

21. The method of claim 20, wherein delivering augmentation therapy includes delivering PESP.

22. The method of claim 21, further comprising delivering ACP contemporaneously with the delivery of the augmentation therapy.

23. The method of claim 22, wherein the ACP includes an AOP offset.

24. The method of claim 20, wherein delivering augmentation therapy includes delivering NES/CCM.

25. The method of claim 24, further comprising delivering AOP contemporaneously with the augmentation therapy.

26. The method of claim 20, wherein delivering augmentation therapy includes delivering NES/CCM and PESP.

27. The method of claim 26, further comprising delivering ACP contemporaneously with the augmentation therapy.

28. The method of claim 27, wherein the ACP includes an AOP offset.

29. The method of claim 20, further comprising:
    determining if an onset of sleep-disordered breathing is occurring; and
    delivering the augmentation therapy prior to the sleep-disordered breathing occurring.

30. The method of claim 20, further comprising:
    determining a mean heart rate oscillation; and
    generating atrial overdrive pacing contemporaneously with the augmentation therapy, wherein an atrial overdrive pacing rate is the determined mean heart rate plus an integer value.

31. The method of claim 20, further comprising:
determining a cycle length of sleep-disordered breathing;
determining mean heart rate oscillation; and
delivering ACP contemporaneously with the augmentation therapy for X cardiac cycles, wherein X is selected based on the determined cycle length and the ACP rate is equal to twice the mean heart rate oscillation plus an integer value causing an AOP offset.

32. The method of claim 20, wherein the X number of cardiac cycles equates to a time interval that is equal to or greater than the cycle length.

33. The method of claim 20, wherein the x number of cardiac cycles equate to a time interval that is equal to or greater than the cycle length.

34. The method of claim 20, further comprising:
detecting an onset of a sleep-disordered breathing episode; and
causing the augmentation therapy to be delivered prior to the episode occuring.

35. The method of claim 20, further comprising:
monitoring a first time value as a heart rate increase beyond a dynamic threshold;
monitoring a second time value of a subsequent occurrence of the heart rate increasing beyond the dynamic threshold;
calculating a final cycle time by subtracting the first time value from the second time value; and
delivering the augmentation therapy for X number of cardiac cycles, wherein X is selected based on the calculated final cycle time.

36. The method of claim 35, wherein X cardiac cycles equate to a time interval that is greater than or equal to the final cycle time.

37. The method of claim 35, wherein multiple episodes of sleep-disordered breathing are monitored, each episode resulting in an individual cycle time so that the final cycle time is an average of the individual cycle times.

38. The method of claim 37, wherein the individual cycle times are discarded if they are shorter than a predetermined minimum value or are longer than a predetermined maximum value.

39. The method of claim 38, wherein the final cycle time is calculated only if the individual cycle times result from consecutive episodes.

40. The method of claim 35, further comprising:
determining a mean sleep disorder heart rate that is the mean value of the heart rate during sleep-disordered breathing; and
generating atrial pacing contemporaneously with the augmentation therapy, wherein an atrial pacing rate is selected based on the mean sleep disorder heart rate.

41. The method of claim 40, wherein the atrial pacing rate is equal to the mean sleep disorder heart rate plus an integer value to achieve AOP.

42. The method of claim 40, wherein the atrial pacing rate is equal to a multiple of the sleep disorder heart rate to achieve ACP.

43. The method of claim 40, wherein the atrial pacing rate is equal to a multiple of the sleep disorder heart rate plus an integer value to achieve ACP with and AOP offset.

44. The method of claim 20, further comprising:
delivering AOP along as a therapy for sleep-disordered breathing and only proceeding to deliver the augmentation therapy if AOP is unsuccessful.

45. The method of claim 20, wherein determining if sleep-disordered breathing is present includes obtaining data from a sensor monitoring a physical parameter.

46. The method of claim 45, wherein the physical parameter is one selected from the group consisting of: respiration rate, minute ventilation, heart rate, neural activity, apnea, hypopnea, hyperventilation, breath sounds, temperature, blood pressure, chest movement, impedance, saturated carbon dioxide, and saturated oxygen.

47. A computer readable medium containing instructions that when implemented, cause an implantable medical device to perform actions to provide therapy for sleep-disordered breathing, the actions comprising:
determining if sleep-disordered breathing is present; and
delivering augmentation therapy in the form of electrical stimulation to cardiac tissue if sleep-disordered breathing is determined to be present;
determining a cycle length for a sleep-disordered breathing episode; and
delivering the augmentation therapy for X number of cardiac cycles, wherein X is selected based on the determined cycle length, wherein the cycle length is an averaged value of multiple sleep-disordered breathing episodes.

48. The computer readable medium of claim 47, wherein delivering augmentation therapy includes delivering PESP.

49. The computer readable medium of claim 48, further comprising delivering ACP contemporaneously with the delivery of the augmentation therapy.

50. The computer readable medium of claim 49, wherein the ACP includes an AOP offset.

51. The computer readable medium of claim 47, wherein delivering augmentation therapy includes delivering NES/CCM.

52. The computer readable medium of claim 51, further comprising delivering AOP contemporaneously with the augmentation therapy.

53. The computer readable medium of claim 47, wherein delivering augmentation therapy includes delivering NES/CCM and PESP.

54. The computer readable medium of claim 53, further comprising delivering ACP contemporaneously with the augmentation therapy.

55. The computer readable medium of claim 54, wherein the ACP includes an AOP offset.

56. The computer readable medium of claim 47, further comprising:
determining if an onset of sleep-disordered breathing is occuring; and
delivering the augmentation therapy prior to the sleep-disordered breathing occuring.

57. The computer readable medium of claim 47, further comprising:
determining a mean heart rate oscillation; and
generating atrial overdrive pacing contemporaneously with the augmentation therapy, wherein an atrial overdrive pacing rate is the determined mean heart rate plus an integer value.

58. The computer readable medium of claim 47, further comprising:
determining a cycle length of sleep-disordered breathing;
determining mean heart rate oscillation; and
delivering ACP contemporaneously with the augmentation therapy for X cardiac cycles, wherein X is selected based on the determined cycle length and the ACP rate is equal to twice the mean heart rate oscillation plus an integer value causing an AOP offset.

59. The computer readable medium of claim 47, wherein the X number of cardiac cycles equates to a time interval that is equal to or greater than the cycle length.

60. The computer readable medium of claim 47, wherein the x number of cardiac cycles equate to a time interval that is equal to or greater than the cycle length.

61. The computer readable medium of claim 47, further comprising:
- detecting an onset of a sleep-disordered breathing episode; and
- causing the augmentation therapy to be delivered prior to the episode occuring.

62. The computer readable medium of claim 47, further comprising:
- monitoring a first time value as a heart rate increase beyond a dynamic threshold;
- monitoring a second time value of a subsequent occurrence of the heart rate increasing beyond the dynamic threshold;
- calculating a final cycle time by subtracting the first time value from the second time value; and
- delivering the augmentation therapy for X number of cardiac cycles, wherein X is selected based on the calculated final cycle time.

63. The computer readable medium of claim 62, wherein X cardiac cycles equate to a time interval that is greater than or equal to the final cycle time.

64. The computer readable medium of claim 62, wherein multiple episodes of sleep-disordered breathing are monitored, each episode resulting in an individual cycle time so that the final cycle time is an average of the individual cycle times.

65. The computer readable medium of claim 64, wherein the individual cycle times are discarded if they are shorter than a predetermined minimum value or are longer than a predetermined maximum value.

66. The computer readable medium of claim 65, wherein the final cycle time is calculated only if the individual cycle times result from consecutive episodes.

67. The computer readable medium of claim 62, further comprising:
- determining a mean sleep disorder heart rate that is the mean value of the heart rate during sleep-disordered breathing; and
- generating atrial pacing contemporaneously with the augmentation therapy, wherein an atrial pacing rate is selected based on the mean sleep disorder heart rate.

68. The computer readable medium of claim 67, wherein the atrial pacing rate is equal to the mean sleep disorder heart rate plus an integer value to achieve AOP.

69. The computer readable medium of claim 67, wherein the atrial pacing rate is equal to a multiple of the sleep disorder heart rate to achieve ACP.

70. The computer readable medium of claim 67, wherein the atrial pacing rate is equal to a multiple of the sleep disorder heart rate plus an integer value to achieve ACP with and AOP offset.

71. The computer readable medium of claim 47, further comprising:
- delivering AOP along as a therapy for sleep-disordered breathing and only proceeding to deliver the augmentation therapy if AOP is unsuccessful.

72. The computer readable medium of claim 47, wherein determining if sleep-disordered breathing is present includes obtaining data from a sensor monitoring a physical parameter.

73. The computer readable medium of claim 72, wherein the physical parameter is one selected from the group consisting of: respiration rate, minute ventilation, heart rate, neural activity, apnea, hypopnea, hyperventilation, breath sounds, temperature, blood pressure, chest movement, impedance, saturated carbon dioxide, and saturated oxygen.

* * * * *